United States Patent [19]
Langer et al.

[11] Patent Number: 6,160,084
[45] Date of Patent: Dec. 12, 2000

[54] BIODEGRADABLE SHAPE MEMORY POLYMERS

[75] Inventors: Robert S. Langer, Newton, Mass.; Andreas Lendlein, Aachen, Germany; Annette Schmidt, Aachen, Germany; Hans Grablowitz, Aachen, Germany

[73] Assignee: Massachusetts Institute of Technology, Cambridge, Mass.

[21] Appl. No.: 09/256,620

[22] Filed: Feb. 23, 1999

Related U.S. Application Data

[60] Provisional application No. 60/075,523, Feb. 23, 1998.

[51] Int. Cl.$^7$ .................................................. C08G 63/02
[52] U.S. Cl. ......................... 528/272; 528/176; 528/193; 528/196; 528/271
[58] Field of Search .................................... 528/176, 193, 528/196, 271, 272

[56] References Cited

U.S. PATENT DOCUMENTS

| | | |
|---|---|---|
| 4,575,373 | 3/1986 | Johnson . |
| 4,596,728 | 6/1986 | Yang et al. . |
| 4,804,733 | 2/1989 | Bataille . |
| 4,816,094 | 3/1989 | Pomplun et al. . |
| 5,049,591 | 9/1991 | Hayashi et al. . |
| 5,108,755 | 4/1992 | Daniels . |
| 5,128,197 | 7/1992 | Kobayashi et al. . |
| 5,139,832 | 8/1992 | Hayashi et al. . |
| 5,145,935 | 9/1992 | Hayashi . |
| 5,189,110 | 2/1993 | Ikematu et al. . |
| 5,418,261 | 5/1995 | Helsemans et al. . |
| 5,506,300 | 4/1996 | Ward et al. . |
| 5,591,786 | 1/1997 | Oxman et al. . |
| 5,635,545 | 6/1997 | Oxman et al. . |
| 5,665,822 | 9/1997 | Bitler et al. . |
| 5,665,831 | 9/1997 | Neuenschwander et al. . |
| 5,765,682 | 6/1998 | Bley et al. . |
| 5,776,162 | 7/1998 | Kleshinski . |
| 5,800,516 | 9/1998 | Fine et al. . |

FOREIGN PATENT DOCUMENTS

| | | |
|---|---|---|
| 42 26 465 A1 | 2/1993 | Germany . |
| WO 95/34331 A1 | 12/1995 | WIPO . |
| WO 98/14803 A1 | 4/1998 | WIPO . |

OTHER PUBLICATIONS

Cederstrom & Van Humbeeck, "Relationship between shape memory material properties and applications," *Journal de Physique IV* 5:C2–335–41 (1995).

Dagani, "Intelligent Gels," *Chemistry & Engineering News* 75:29–37 (1997).

Echigo, et al., "Development of a new transvenous patent ductus arteriosus occlusion technique using a shape memory polymer," *ASAIO Trans.* 36(3):M195–8 (1990).

Gordon, "Applications of Shape Memory Polyurethanes," *Proceedings of the First International Conference on Shape Memory and Superelastic Technologies, SMST International Committee*, pp. 115–19 (1994).

(List continued on next page.)

*Primary Examiner*—Terressa M. Boykin
*Attorney, Agent, or Firm*—Arnall Golden & Gregory, LLP

[57] ABSTRACT

Biodegradable shape memory polymer compositions, articles of manufacture thereof, and methods of preparation and use thereof are described. In one embodiment the compositions include at least one hard segment and at least one soft segment. The $T_{trans}$ of the hard segment is preferably between –30 and 270° C. At least one of the hard or soft segments can contain a crosslinkable group, and the segments can be linked by formation of an interpenetrating network or a semi-interpenetrating network, or by physical interactions of the segments. Objects can be formed into a given shape at a temperature above the $T_{trans}$ of the hard segment, and cooled to a temperature below the $T_{trans}$ of the soft segment. If the object is subsequently formed into a second shape, the object can return to its original shape by heating the object above the $T_{trans}$ of the soft segment and below the $T_{trans}$ of the hard segment.

26 Claims, 5 Drawing Sheets

OTHER PUBLICATIONS

Hayashi, et al., "Properties and applications of polyurethane–series shape memory polymer," *ANTEC* 1998–2001 (1994).

He, et al., "Higher order structure and thermo–responsive properties of polymeric gel with crystalline side chains," *Polymer Journal* 28:452–7 (1996).

Ito, et al, "Variation of free volume size and contenct of shape memory polymer–polyurethane–upon temperature studied by positron annihilation lifetime techniques and infared spectroscopy," *J. Radioanalytical and Nuc. Chem.* 211:53–60 (1996).

Kagami, et al., "Shape memory behaviors of crosslinked copolymers containing strearyl acrylate," *Macromol, Rapid Commun.* 17:539–543 (1996).

Kim, et al., "Polyurethanes having shape memory effect," *Polymer* 37(26):5781–93 (1996).

Li, et al., "Crystallinity and morphology of segmented polyurethanes with diferent soft–segment length," *J. Applied Polymer* 62:631–38 (1996).

Linge & Dahm, "Praktische aspekte der verwendung von superelastischen drahtbogen in der edgewisetechnik," *Forschr. Kieferorthop* 55:324–329 (1994).

Nakasima, et al., "Potential application of shape memory plastic as elastic material in clinical orthodontics," *Eur. J. of Ortho.* 13:179–186 (1991).

Sakurai, et al., "Crystal trsnformation of styrene–butadiene block coplymer," *Polymer* 35:4288–9 (1992).

Takahashi, et al. "Structure and properties of shape–memory polyurethane block copolymers," *J. Applied Polymer Science* 60:1061–69 (1996).

Tobushi, et al., "Mechanical properties of shape memory polymer of polyurethane series," *JSME International Journal Series I* 35:296–302 (1992).

Tobushi, et al., "Theromomechanical properties in a thin film of shape memory polymer of polyurethane series," *SPIE* 2716:46–57 (1996).

White & Ward, "Softenable, shape–memory thermoplastic for use in biomedical devices," *Mat. Res. Soc. Symp. Proc.* 110:635–640 (1989).

P = THERMOPLASTIC MATERIALS

SOFT SEGMENT           HARD SEGMENT

O - JUNCTION UNIT

P0 - SEMICRYSTALLINE HOMOPOLYMERS, SEMICRYSTALLINE
     COPOLYMERS AND BLENDS THEREOF

P1 - THERMOPLASTIC ELASTOMERS WITH LINEAR CHAINS

P2 - THERMOPLASTIC ELASTOMERS WITH SIDE CHAINS OR ANY KIND
     OF DENDRITIC STRUCTURAL ELEMENTS

BIODEGRADABLE SHAPE MEMORY POLYMERS

CROSS REFERENCE TO RELATED APPLICATIONS

Priority is claimed to U.S. Provisional application Ser. No. 60/075,523, filed Feb. 23, 1998.

BACKGROUND OF THE INVENTION

This application is generally in the area of shape memory polymers, and more particularly to biodegradable shape memory polymers.

Figure 1:
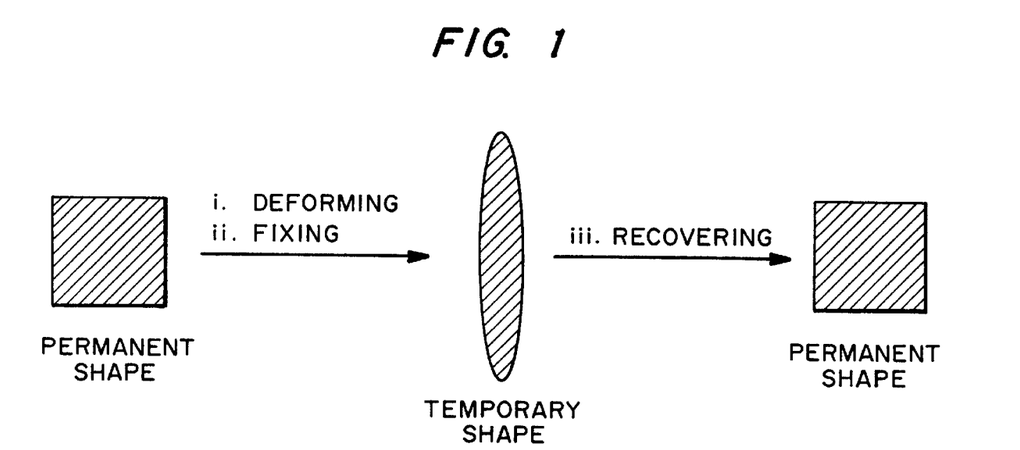
FIG. 1 is an illustration of the one-way shape memory effect.
Figure 2:
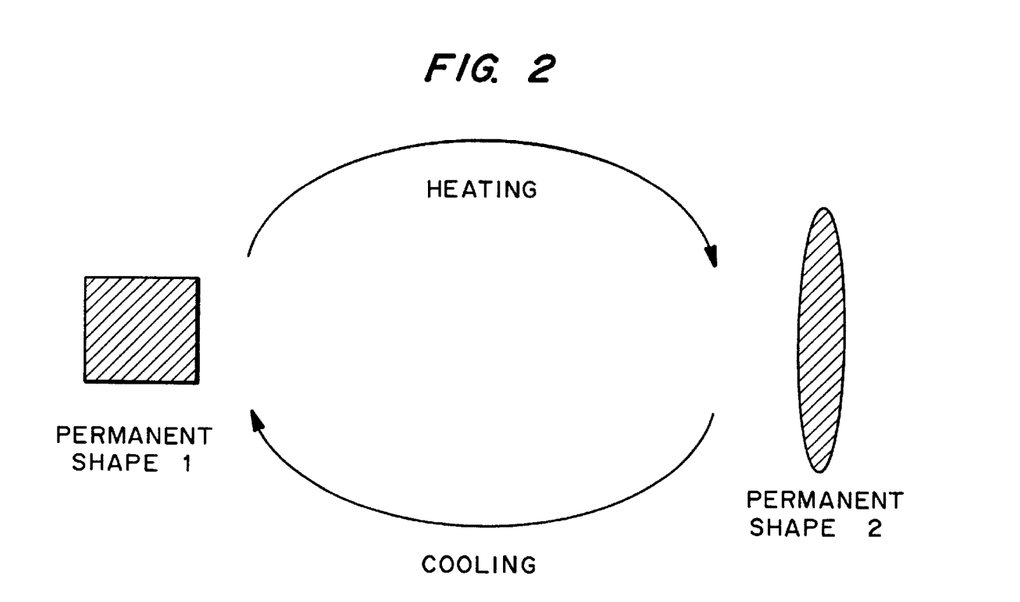
FIG. 2 is an illustration of the two-way (thermal) shape memory effect.

Shape memory is the ability of a material to remember its original shape, either after mechanical deformation (FIG. 1), which is a one-way effect, or by cooling and heating (FIG. 2), which is a two-way effect. This phenomenon is based on a structural phase transformation.

The first materials known to have these properties were shape memory metal alloys (SMAs), including TiNi (Nitinol), CuZnAl, and FeNiAl alloys. The structure phase transformation of these materials is known as a martensitic transformation. These materials have been proposed for various uses, including vascular stents, medical guidewires, orthodontic wires, vibration dampers, pipe couplings, electrical connectors, thermostats, actuators, eyeglass frames, and brassiere underwires. These materials have not yet been widely used, in part because they are relatively expensive.

Shape memory polymers (SMPs) are being developed to replace or augment the use of SMAs, in part because the polymers are light, high in shape recovery ability, easy to manipulate, and economical as compared with SMAs. In the literature, SMPs are generally characterized as phase segregated linear block co-polymers having a hard segment and a soft segment. The hard segment is typically crystalline, with a defined melting point, and the soft segment is typically amorphous, with a defined glass transition temperature. In some embodiments, however, the hard segment is amorphous and has a glass transition temperature rather than a melting point. In other embodiments, the soft segment is crystalline and has a melting point rather than a glass transition temperature. The melting point or glass transition temperature of the soft segment is substantially less than the melting point or glass transition temperature of the hard segment.

When the SMP is heated above the melting point or glass transition temperature of the hard segment, the material can be shaped. This (original) shape can be memorized by cooling the SMP below the melting point or glass transition temperature of the hard segment. When the shaped SMP is cooled below the melting point or glass transition temperature of the soft segment while the shape is deformed, a new (temporary) shape is fixed. The original shape is recovered by heating the material above the melting point or glass transition temperature of the soft segment but below the melting point or glass transition temperature of the hard segment. In another method for setting a temporary shape, the material is deformed at a temperature lower than the melting point or glass transition temperature of the soft segment, resulting in stress and strain being absorbed by the soft segment. When the material is heated above the melting point or glass transition temperature of the soft segment, but below the melting point (or glass transition temperature) of the hard segment, the stresses and strains are relieved and the material returns to its original shape. The recovery of the original shape, which is induced by an increase in temperature, is called the thermal shape memory effect.

Properties that describe the shape memory capabilities of a material are the shape recovery of the original shape and the shape fixity of the temporary shape.

Several physical properties of SMPs other than the ability to memorize shape are significantly altered in response to external changes in temperature and stress, particularly at the melting point or glass transition temperature of the soft segment. These properties include the elastic modulus, hardness, flexibility, vapor permeability, damping, index of refraction, and dielectric constant. The elastic modulus (the ratio of the stress in a body to the corresponding strain) of an SMP can change by a factor of up to 200 when heated above the melting point or glass transition temperature of the soft segment. Also, the hardness of the material changes dramatically when the soft segment is at or above its melting point or glass transition temperature. When the material is heated to a temperature above the melting point or glass transition temperature of the soft segment, the damping ability can be up to five times higher than a conventional rubber product. The material can readily recover to its original molded shape following numerous thermal cycles, and can be heated above the melting point of the hard segment and reshaped and cooled to fix a new original shape.

Conventional shape memory polymers generally are segmented polyurethanes and have hard segments that include aromatic moieties. U.S. Pat. No. 5,145,935 to Hayashi, for example, discloses a shape memory polyurethane elastomer molded article formed from a polyurethane elastomer polymerized from of a difunctional diiiosicyanate, a difunctional polyol, and a difunctional chain extender.

Examples of polymers used to prepare hard and soft segments of known SMPs include various polyethers, polyacrylates, polyamides, polysiloxanes, polyurethanes, polyether amides, polyurethane/ureas, polyether esters, and urethane/butadiene copolymers. See, for example, U.S. Pat. No. 5,506,300 to Ward et al.; U.S. Pat. No. 5,145,935 to Hayashi; U.S. Pat. No. 5,665,822 to Bitler et al.; and Gorden, "Applications of Shape Memory Polyurethanes," *Proceedings of the First International Conference on Shape Memory and Superelastic Technologies, SMST International Committee*, pp. 115–19 (1994).

Although these polymers have been proposed for a number of uses, their medical applications have been limited to devices which are not implanted or left in the body. It is desirable to have shape memory polymers, but which are biodegradable. Many other applications for biodegradable shape memory polymers are apparent, for example, for use in making diaper or medical drape linings, or in packagings for food or other materials where there are disposal problems. It is not apparent from the commercially available polyurethane materials that one could incorporate biodegradable materials into a shape memory polymer, and retain the structural and other phyical and chemical properties which are essential to shape memory polymers and their application. Moreover, the components of the known polyurethane shape memory polymers contain aromatic groups which would be expected to not be biocompatible.

It is therefore an object of the present invention to provide biodegradable shape memory polymers.

It is still a further object of the present invention to provide shape memory polymers with physical and chemical properties and chemical structures that are different than those in conventional shape memory polymers.

SUMMARY OF THE INVENTION

Biodegradable shape memory polymer compositions, articles of manufacture thereof, and methods of preparation and use thereof are described. The polymer compositions include one or more hard segments and one or more soft segments, wherein the compositions are biocompatible and at least one of the segments is biodegradable or at least one of the segments is linked to another segment via a biodegradable linkage.

The melting point or glass transition temperature (hereinafter, the $T_{trans}$) of the hard segment is at least 10° C., and preferably 20° C., higher than the $T_{trans}$ of the soft segment. The $T_{trans}$ of the hard segment is preferably between −30 and 270° C., and more preferably between 30 and 150° C. The ratio by weight of the hard segment:soft segments is between about 5:95 and 95:5, preferably between 20:80 and 80:20. The shape memory polymers contain at least one physical crosslink (physical interaction of the hard segment) or contain covalent crosslinks instead of a hard segment. The shape memory polymers can also be interpenetrating networks or a semi-interpenetrating networks.

In addition to changes in state from a solid to liquid state (melting point or glass transition temperature), hard and soft segments may undergo solid to solid state transitions, and can undergo ionic interactions involving polyelectrolyte segments or supramolecular effects based on highly organized hydrogen bonds.

Any polymers that are crystalline or amorphous and that have a $T_{trans}$ within the range defined herein can be used to form the hard and soft segments. Representative biodegradable polymers include polyhydroxy acids, polyalkanoates, polyanhydrides, polyphosphazenes, polyetheresters, polyesteramides, polyesters, and polyorthoesters. Exemplary biodegradable linkages include ester, amide, anhydride, carbonate, and orthoester linkages.

Articles of manufacture can be prepared from the shape memory polymer compositions, for example, by injection molding, blowing, extrusion, and laser ablation. To prepare an object having a shape in memory, the object can be formed at a temperature above the $T_{trans}$ of the hard segment, and cooled to a temperature below the $T_{trans}$ of the soft segment. If the object subsequently is formed into a second shape, the object can be returned to its original shape by heating the object above the $T_{trans}$ of the soft segment and below the $T_{trans}$ of the hard segment.

Thermoset polymers can be prepared by pre-shaping macromonomers, for example, by extrusion, and fix-ing the original shape at a temperature above the $T_{trans}$ of the thermoset polymer, for example, by photocuring reactive groups on the macromonomer.

DETAILED DESCRIPTION OF THE INVENTION

Biodegradable shape memory polymer compositions, articles of manufacture thereof, and methods of preparation and use thereof are described.

Definitions

As used herein, the term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used herein in reference to polymers, the term "degrade" refer to cleavage of the polymer chain, such that the molecular weight stays approximately constant at the oligomer level and particles of polymer remain following degradation. The term "completely degrade" refers to cleavage of the polymer at the molecular level such that there is essentially complete mass loss. The term "degrade" as used herein includes "completely degrade" unless otherwise indicated.

A polymer is a shape memory polymer if the original shape of the polymer is recovered by heating it above a shape recovering temperature (defined as the $T_{trans}$ of a soft segment) even if the original molded shape of the polymer is destroyed mechanically at a lower temperature than the shape recovering temperature, or if the memorized shape is recoverable by application of another stimulus.

As used herein, the term "segment" refers to a block or sequence of polymer forming part of the shape memory polymer.

As used herein, the terms hard segment and soft segment are relative terms, relating to the $T_{trans}$ of the segments. The hard segment(s) has a higher $T_{trans}$ than the soft segment(s).

The shape memory polymers can include at least one hard segment and at least one soft segment, or can include at least one kind of soft segment wherein at least one kind of the soft segments are crosslinked, without the presence of a hard segment.

The hard segments can be linear oligomers or polymers, and can be cyclic compounds, such as crown ethers, cyclic di-, tri-, or oligopetides, and cyclic oligo(ester amides).

The physical interaction between hard segments can be based on charge transfer complexes, hydrogen bonds, or other interactions, since some segments have melting temperatures that are higher than the degradation temperature. In these cases, there is no melting or glass transition temperature for the segment. A non-thermal mechanism, such as a solvent, is required to change the segment bonding.

The ratio by weight of the hard segment:soft segments is between about 5:95 and 95:5, preferably between 20:80 and 80:20.

Shape Memory Polymeric Compositions

Thermoplastic shape memory materials are shaped/molded to a desired shape above the $T_{trans}$ of the hard segment(s) and cooled down to a temperature below the shape recovering temperature, where the polymer may undergo mechanical deformation and strains are generated in the polymer. The original shape of the deformed polymers are recovered by heating them to a temperature higher than their shape recovering temperature. Above this temperature, the strains in the polymer are relieved, allowing the polymer to return to its original shape. In contrast, thermoset shape memory materials are shaped/molded to a desired shape before the macromonomers used to form the thermoset polymers are polymerized. After the shape has been fixed, the macromonomers are polymerized.

The polymer compositions are preferably compressible by at least one percent or expandable by at least five one of the original thickness at a temperature below the shape recovering temperature, with the deformation being fixed by application of a stimulus such as heat, light, ultrasound, magnetic fields or electric fields. In some embodiments, the materials show a ratio of recovery of 98% (compare to experimental examples).

When significant stress is applied, resulting in an enforced mechanical deformation at a temperature lower than the shape recovering temperature, strains are retained in the soft segments or amorphous regions, and bulky shape change is kept even after the partial liberation of strain by the elasticity of the polymer. If the configuration of the molecular chains is disturbed by influencing the regulated arrangement of molecular chains at a temperature lower than the glass transition temperature, rearrangement of the molecular chains is assumed to occur through the increase of the volume size and the decrease of the free volume content. The original shape is recovered by the contraction of the hard segment aggregates by the elevation of the temperature according to rigid control of chain conformations and the shape of the polymer is restored to the memorized shape.

In addition to changes in state from a solid to liquid state (melting point or glass transition temperature), hard or soft segments can undergo ionic interactions involving polyelectrolyte segments or supramolecular effects based on highly organized hydrogen bonds. The SM polymer can also undergo solid state to solid state transitions (e.g. change in morphology). Solid state to solid state transitions are well known to those of skill in the art, e.g. in poly(styrene-block-butadiene).

Various changes can take place to the structure of an object formed using the shape memory polymers. If the objects are three dimensional objects, the changes in shape can be two dimensional. If the objects are essentially two dimensional objects, such as fibers, then the changes in shape can be one dimensional, such as along the length. The thermal and electrical conductivity of the materials can also change in response to changes in temperature.

The moisture permeability of the compositions can be varied, especially when the polymer is formed into a thin film (i.e., less than about 10 $\mu$m). Some polymer compositions, in their original shape, have a sufficient permeability such that molecules of water vapor can be transmitted through the polymer film, while water molecules are not large enough to penetrate the polymer film. The resulting materials have low moisture permeability at temperatures below room temperature and high moisture permeability at temperatures above room temperature.

Stimuli other than temperature can be used to induce shape changes. As described with reference to certain embodiments below, the shape changes can be elicited by exposure to light activation or an agent such as an ion which alters the interpolymer bonds.

I. Polymer Segments

The segments preferably are oligomers. As used herein, the term "oligomer" refers to a linear chain molecule having a molecular weight up to 15,000 Da.

The polymers are selected based on the desired glass transition temperature(s) (if at least one segment is amorphous) or the melting point(s) (if at least one segment is crystalline), which in turn is based on the desired applications, taking into consideration the environment of use. Preferably, the number average molecular weight of the polymer block is greater than 400, and is preferably in the range of between 500 and 15,000.

The transition temperature at which the polymer abruptly becomes soft and deforms can be controlled by changing the monomer composition and the kind of monomer, which enables one to adjust the shape memory effect at a desired temperature.

The thermal properties of the polymers can be detected, for example, by dynamic mechanical thermoanalysis or differential scanning calorimetry (DSC) studies. In addition the melting point can be determined using a standard melting point apparatus.

1. Thermoset or thermoplastic polymers.

The polymers can be thermoset or thermoplastic polymers, although thermoplastic polymers may be preferred due to their ease of molding.

Preferably, the degree of crystallinity of the polymer or polymeric block(s) is between 3 and 80%, more preferably between 3 and 60%. When the degree of crystallinity is greater than 80% while all soft segments are amorphous, the resulting polymer composition has poor shape memory characteristics.

The tensile modulus of the polymers below the $T_{trans}$ is typically between 50 MPa and 2 GPa (gigapascals), whereas the tensile modulus of the polymers above the $T_{trans}$ is typically between 1 and 500 MPa. Preferably, the ratio of elastic modulus above and below the $T_{trans}$ is 20 or more. The higher the ratio, the better the shape memory of the resulting polymer composition.

The polymer segments can be natural or synthetic, although synthetic polymers are preferred. The polymer segments can be biodegradable or non-biodegradable, although the resulting SMP composition is biodegradable biocompatible polymers are particularly preferred for medical applications. In general, these materials degrade by hydrolysis, by exposure to water or enzymes under physiological conditions, by surface erosion, bulk erosion, or a combination thereof. Non-biodegradable polymers used for medical applications preferably do not include aromatic groups, other than those present in naturally occurring amino acids.

Representative natural polymer segments or polymers include proteins such as zein, modified zein, casein, gelatin, gluten, serum albumin, and collagen, and polysaccharides such as alginate, celluloses, dextrans, pullulane, and polyhyaluronic acid, as well as chitin, poly(3-hydroxyalkanoate)s, especially poly($\beta$-hydroxybutyrate), poly(3-hydroxyoctanoate) and poly(3-hydroxyfatty acids).

Representative natural biodegradable polymer segments or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Representative synthetic polymer blocks include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. These are collectively referred to herein as "celluloses".

Representative synthetic degradable polymer segments or polymers include polyhydroxy acids, such as polylactides, polyglycolides and copolymers thereof; poly(ethylene terephthalate); poly(hydroxybutyric acid); poly(hydroxyvaleric acid); poly[lactide-co-($\epsilon$-caprolactone)]; poly[glycolide-co-($\epsilon$-caprolactone)]; polycarbonates, poly(pseudo amino acids); poly(amino acids); poly(hydroxyalkanoate)s; polyanhydrides; polyortho esters; and blends and copolymers thereof.

Examples of non-biodegradable polymer segments or polymers include ethylene vinyl acetate, poly(meth)acrylic acid, polyamides, polyethylene, polypropylene, polystyrene, polyvinyl chloride, polyvinylphenol, and copolymers and mixtures thereof.

Rapidly bioerodible polymers such as poly(lactide-co-glycolide)s, polyanhydrides, and polyorthoesters, which have carboxylic groups exposed on the external surface as the smooth surface of the polymer erodes, also can be used. In addition, polymers containing labile bonds, such as polyanhydrides and polyesters, are well known for their hydrolytic reactivity. Their hydrolytic degradation rates can generally be altered by simple changes in the polymer backbone and their sequence structure.

Various polymers, such as polyacetylene and polypyrrole, are conducting polymers. These materials are particularly preferred for uses in which electrical conductance is important. Examples of these uses include tissue engineering and any biomedical application where cell growth is to be stimulated. These materials may find particular utility in the field of computer science, as they are able to absorb heat without increasing in temperature better than SMAs. Conducting shape memory polymers are useful in the field of tissue engineering to stimulate the growth of tissue, for example, nerve tissue.

2. Hydrogels.

The polymer may be in the form of a hydrogel (typically absorbing up to about 90% by weight of water), and can optionally be ionically crosslinked with multivalent ions or polymers. Ionic crosslinking between soft segments can be used to hold a structure, which, when deformed, can be reformed by breaking the ionic crosslinks between the soft segments. The polymer may also be in the form of a gel in solvents other than water or aqueous solutions. In these polymers, the temporary shape can be fixed by hydrophilic interactions between soft segments.

Hydrogels can be formed from polyethylene glycol, polyethylene oxide, polyvinyl alcohol, polyvinyl pyrrolidone, polyacrylates, poly (ethylene terephthalate), poly(vinyl acetate), and copolymers and blends thereof. Several polymeric segments, for example, acrylic acid, are elastomeric only when the polymer is hydrated and hydrogels are formed. Other polymeric segments, for example, methacrylic acid, are crystalline and capable of melting even when the polymers are not hydrated. Either type of polymeric block can be used, depending on the desired application and conditions of use.

For example, shape memory is observed for acrylic acid copolymers only in the hydrogel state, because the acrylic acid units are substantially hydrated and behave like a soft elastomer with a very low glass transition temperature. The dry polymers are not shape memory polymers. When dry, the acrylic acid units behave as a hard plastic even above the glass transition temperature and show no abrupt change in mechanical properties on heating. In contrast, copolymers including methyl acrylate polymeric segments as the soft segments show shape memory properties even when dry.

3. Polymers Capable of Forming a Gel at Increased Temperatures.

Certain polymers, for example, poly(ethylene oxide-co-propylene oxide) (PLURONICS™), are soluble in water at temperatures lower than body temperature and become hydrogels at temperatures higher than body temperature. Incorporation of these polymers as segments in shape memory polymers provides them with the ability to response to changes in temperature in a manner opposite that of typical shape memory polymers. These materials recover their shape when cooled below their shape recovery temperature, rather than being heated above their shape recovery temperature. This effect is called inversed thermal shape memory effect. Shape memory polymer compositions including these polymer segments are useful in various biomedical applications where the polymer can be inserted as a liquid, and cooled to recover an intended shape in situ. The inverse thermal shape memory effect can be obtained by incorporating two different segments into a polymer that are miscible at temperatures lower than $T_{misc}$, but are immiscible at higher temperatures. The phase separation at higher temperatures stabilizes the temporary shape.

The polymers can be obtained from commercial sources such as Sigma Chemical Co., St. Louis, Mo.; Polysciences, Warrenton, Pa.; Aldrich Chemical Co., Milwaukee, Wis.; Fluka, Ronkonkoma, N.Y.; and BioRad, Richmond, Calif. Alternately, the polymers can be synthesized from monomers obtained from commercial sources, using standard techniques.

II. Assembly of Polymer Segments

The shape memory polymer include one or more hard segments and one or more soft segments, wherein at least one of the segments is biodegradable or at least one of the segments is linked to another segment via a biodegradable linkage. Representative biodegradable linkages include ester-, amide-, anhydride-, carbonate-, or orthoester linkages.

1. Polymer Structures.

The shape memory effect is based on the polymer morphology. With respect to thermoplastic elastomers, the original shape of an object is fixed by physical crosslinks caused by the hard segment. With respect to thermoset polymers, the soft segments are covalently crosslinked instead of having hard segments. The original shape is set by the crosslinking process.

In contrast to prior art segmented polyurethane SMPs, the segments of the compositions described herein need not be linear. The segments can be partially grafted or attached in dendremeric side groups.

A. Thermoplastic and Thermoelastic Polymers

Figure 3:
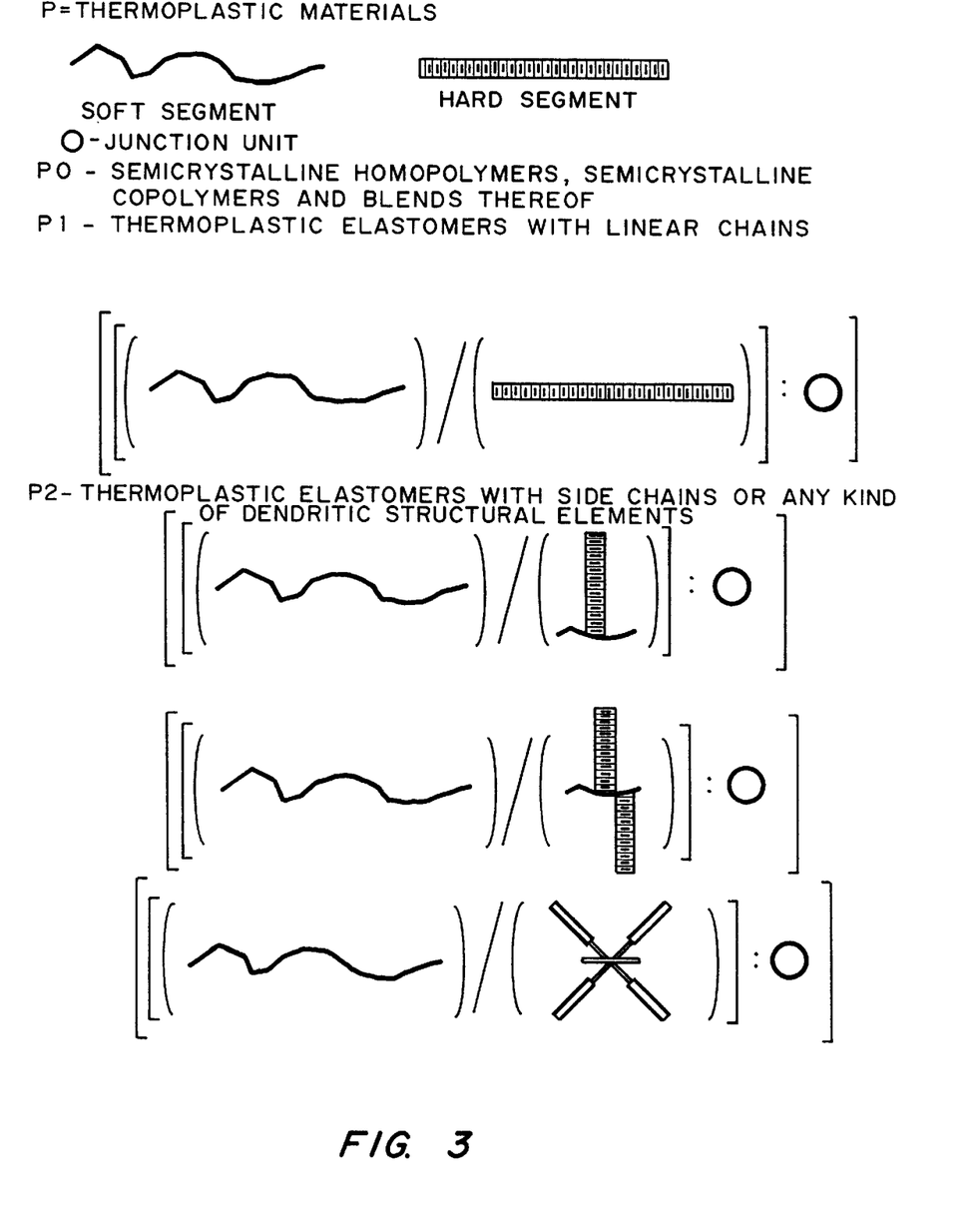
FIG. 3 is an illustration of combinations of suitable classes of thermoplastic materials.

The polymers can be in the form of linear diblock-, triblock-, tetrablock, or multiblock copolymers, branch or graft polymers, thermoplastic elastomers, which contain dendritic structures, and blends thereof. FIG. 3 illustrates some of the combinations of suitable classes of thermoplastic materials forming the hard and soft segments. The thermoplastic shape memory polymer composition also can be a blend of one or more homo- or co-polymer with one or more diblock-, triblock-, tetrablock, or multiblock copolymers, branch or graft polymers. These types of polymers are well known to those of skill in the art.

As used herein, the term "degradable thermoset" refers to (i) thermosets SMPs containing only one soft segment, which contains cleavable bonds, and (ii) thermosets containing more than one soft segment, wherein at least one soft segment is degradable or wherein the different soft segments are connected by cleavable bonds. There are four different types of thermoset polymers that have shape memory capability. These include polymer networks, semi-interpenetrating networks, interpenetrating networks, and mixed-interpenetrating networks.

i. Polymer Networks

A polymer network is prepared by covalently crosslinking macromonomers, i.e., polymers which contain polymerizable endgroups such as carbon-carbon double bonds. The polymerization process can be induced by using light or heat sensitive initiators or by curing with ultraviolet light ("UV-light") without an initiator. Shape memory polymer networks are prepared by crosslinking one or more soft segments which correspond to one or more thermal transitions.

Figure 4:
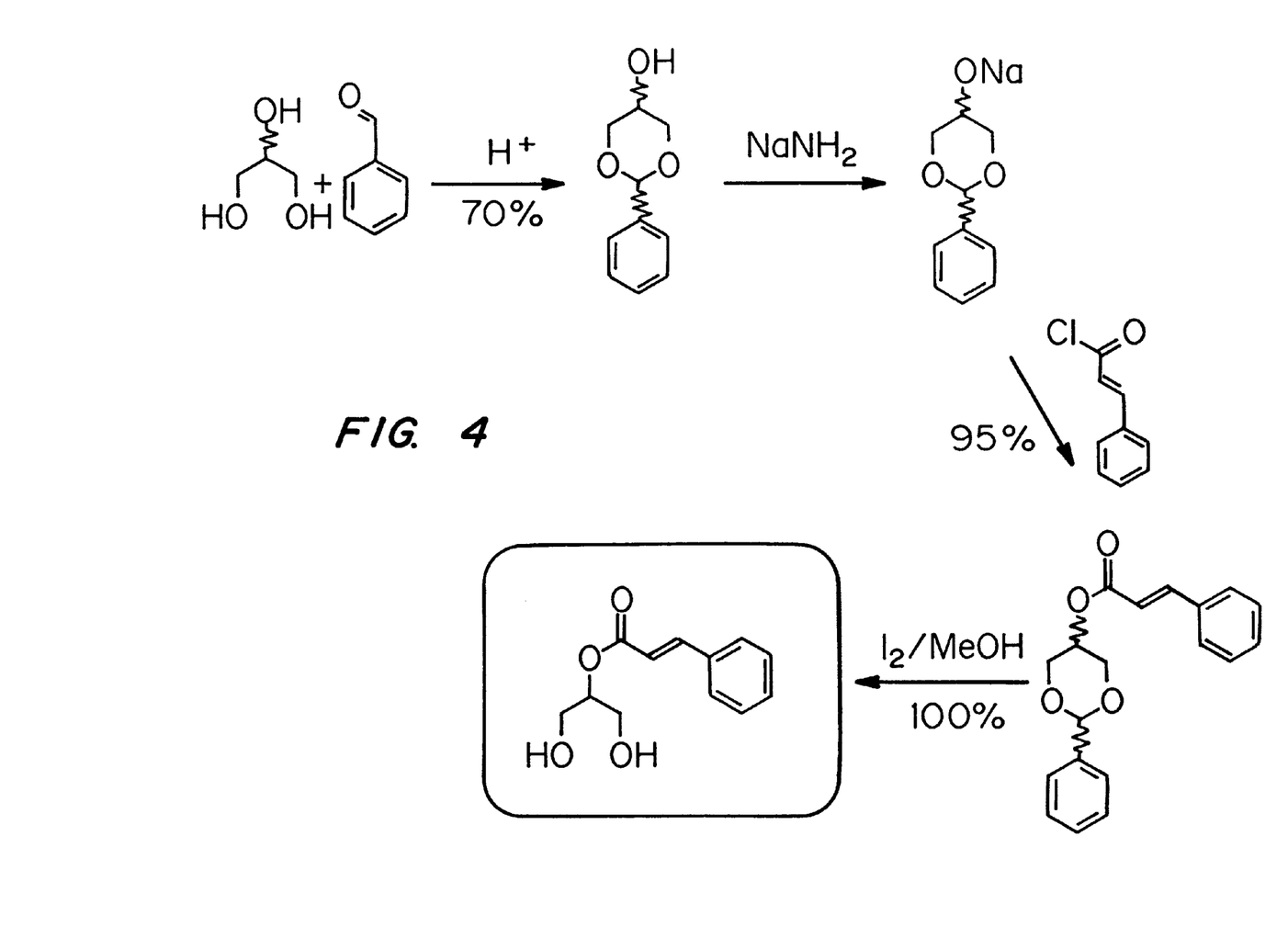
FIG. 4 is a diagram of a reaction sequence for the synthesis of a preferred photocrosslinker.

In an embodiment preferred for biomedical applications, the crosslinking is performed using a photocrosslinker and requires no chemical initiator. The photocrosslinker advantageously eliminates the need for initiator molecules, which may be toxic. FIG. 4 is a diagram of a reaction sequence for the synthesis of a preferred photocrosslinker, which produces an overall yield of about 65%.

ii. Interpenetrating Networks

Interpenetrating networks ("IPN") are defined as networks where two components are crosslinked, but not to each other. The original shape is determined by the network with the highest crosslink density and the highest mechanical strength. The material has at least two $T_{trans}$ corresponding to the different soft segments of both networks.

iii. Mixed Interpenetrating Network

A mixed IPN includes at least one physically crosslinked polymer network (a thermoplastic polymer) and at least one covalently crosslinked polymer network (a thermoset polymer) that cannot be separated by any physical methods. The original shape is set by the covalently crosslinked network. The temporary shapes correspond to the $T_{trans}$ of the soft segments and the $T_{trans}$ of the hard segment of the thermoplastic elastomer component.

A particularly preferred mixed interpenetrating network is prepared by polymerizing a reactive macromonomer in the presence of a thermoplastic polymer, for example, by the photopolymerization of carbon-carbon double bonds. In this embodiment, the ratio by weight of thermoset polymer to thermoplastic polymer is preferably between 5:95 and 95:5, more preferably, between 20:80 and 80:20.

iv. Semi-Interpenetrating Networks

Semi-interpenetrating networks ("semi-IPN") are defined as two independent components, where one component is a crosslinked polymer (a polymer network) and the other component is a non-crosslinked polymer (a homopolymer or copolymer), wherein the components cannot be separated by physical methods. The semi-IPN has at least one thermal transition corresponding to the soft segment(s) and the homo- or co-polymer components. The crosslinked polymer preferably constitutes between about 10 and 90% by weight of the semi-interpenetrating network composition.

v. Polymer Blends

In a preferred embodiment, the shape memory polymer compositions described herein are formed of a biodegradable polymer blend. As used herein, a "biodegradable polymer blend" is a blend having at least one biodegradable polymer.

The shape memory polymers can exist as physical mixtures of thermoplastic polymers. In one embodiment, a shape memory polymer composition can be prepared by interacting or blending two thermoplastic polymers. The polymers can be semicrystalline homopolymers, semicrystalline copolymers, thermoplastic elastomers with linear chains, thermoplastic elastomers with side chains or any kind of dendritic structural elements, and branched copolymers, and these can be blended in any combination thereof.

For example, a multiblock copolymer with a hard segment with a relatively high $T_{trans}$ and a soft segment with a relatively low $T_{trans}$ can be mixed or blended with a second multiblock copolymer with a hard segment with a relatively low $T_{trans}$ and the same soft segment as that in the first multiblock copolymer. The soft segments in both multiblock copolymers are identical, so the polymers are miscible in each other when the soft segments are melted. There are three transition temperatures in the resulting blend—that of the first hard segment, that of the second hard segment, and that of the soft segment. Accordingly, these materials are able to memorize two different shapes. The mechanical properties of these polymers can be adjusted by the changing the weight ratio of the two polymers.

Other kinds of blends of at least two multiblock copolymers, in which at least one of the segments is miscible with at least one of the segments of the other multiblock copolymers, can be prepared. If two different segments are miscible and build one domain together, then the thermal transition of this domain depends on the weight content of the two segments. The maximum number of memorized shapes results from the number of thermal transitions of the blend.

Shape memory blends may have better shape memory capabilities than the blend components alone. Shape memory blends are composed of at least one multiblock copolymer and at least one homo- or copolymer. In principle di-, tri, tetra-block copolymers can be used instead of a multiblock copolymer.

Shape memory blends are highly useful in industrial applications, since a broad range of mechanical, thermal, and shape memory capabilities can be obtained from only two or three basic polymers by blending them in different weight ratios. A twin screw extruder is an example of standard process equipment that could be used to mix the components and process the blend.

III. Methods of Making the SMPs

The polymers described above are either commercially available or can be synthesized using routine chemistry. Those of skill in the art can readily prepare the polymers using known chemistry. Examples 1 and 2 below describe experimental procedures used to prepare the SMPs.

IV. Methods of Shaping the SMP Compositions

The compositions can be formed into a first shape under appropriate conditions, for example, at a temperature above the $T_{trans}$ of the hard segments, and allowed to cool below the $T_{trans}$ of the soft segment(s). Standard techniques are extrusion and injection molding. Optionally, the object can be re-formed into a second shape. Upon application of heat or other appropriate set of conditions, the object returns to original shape.

Figure 5:
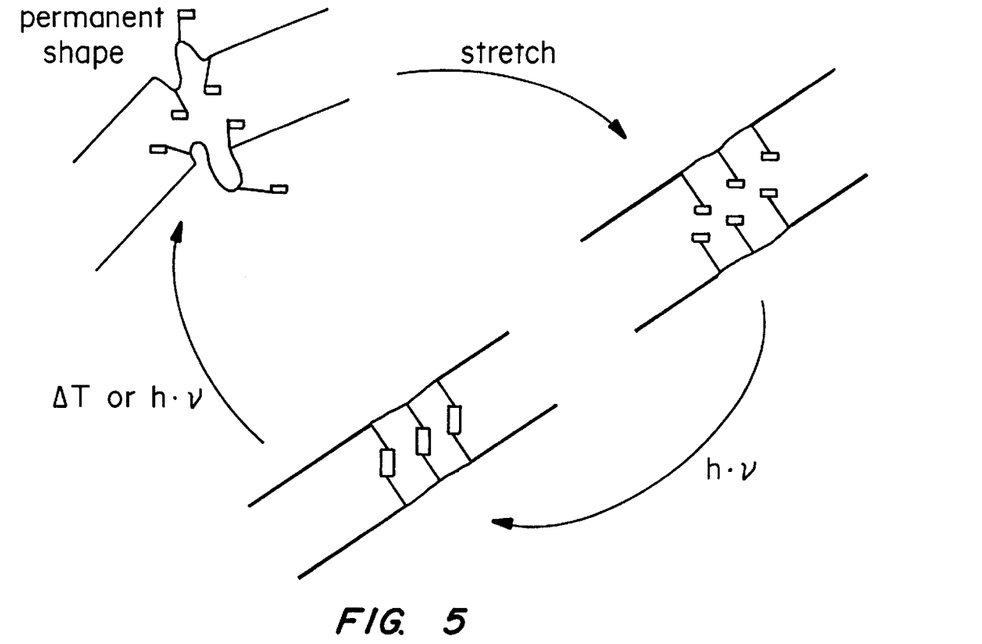
FIG. 5 is an illustration of a photoinduced shape memory effect.

Thermoset polymers can be prepared by extruding the pre-polymerized material (macromonomers), and fixing the original shape at a temperature above the $T_{trans}$ of the thermoset polymer, for example, by photocuring reactive groups on the monomer. The temporary shape is fixed by cooling the material below $T_{trans}$ after deforming the material. FIG. 5 illustrates a photoinduced shape memory effect.

The crosslinking also can be performed in a solution of the macromonomers. The solvent is removed from the formed gel in a subsequent step.

Those compositions formed of thermoplastic polymers can be blown, extruded into sheets or shaped by injection molding, for example, to form fibers. The compositions can also be shaped by other methods known to those of skill in the art for shaping solid objects, for example, laser ablation, micromachining, use of a hot wire, and by CAD/CAM (computer aided design/computer aided manufacture) processes. These processes are preferred for shaping thermoset polymers.

V. Therapeutic, Prophylactic, and Diagnostic Applications

Any of a variety of therapeutic, prophylactic and/or diagnostic agents can be incorporated within the polymer compositions, which can locally or systemically deliver the incorporated agents following administration to a patient.

1. Therapeutic. Diagnostic and Prophylactic Applications

Any of a variety of therapeutic agents can be incorporated within the particles, for local or systemic delivery of the incorporated agents following administration to a patient. Examples include synthetic inorganic and organic compounds or molecules, proteins and peptides, polysaccharides and other sugars, lipids, and nucleic acid molecules having therapeutic, prophylactic or diagnostic activities. Nucleic acid molecules include genes, plasmid DNA, naked DNA, antisense molecules which bind to complementary DNA to inhibit transcription, ribozymes and ribozyme guide sequences. The agents to be incorporated can have a variety of biological activities, such as vasoactive agents, neuroactive agents, hormones, growth factors, cytokines, anaesthetics, steroids, anticoagulants, anti-inflammatories, immunomodulating agents, cytotoxic agents, prophylactic agents, antibiotics, antivirals, antisense, antigens, and antibodies. In some instances, the proteins may be antibodies or antigens which otherwise would have to be administered by injection to elicit an appropriate response. Proteins are defined as consisting of 100 amino acid residues or more; peptides are less than 100 amino acid residues. Unless otherwise stated, the term protein refers to both proteins and peptides. Polysaccharides, such as heparin, can also be administered. Compounds with a wide range of molecular weight, for example, between 10 and 500,000 grams per mole, can be encapsulated.

Imaging agents which may be utilized include commercially available agents used in positron emission tomography (PET), computer assisted tomography (CAT), single photon emission computerized tomography, x-ray, fluoroscopy, magnetic resonance imaging (MRI), and ultrasound agents.

VI. Articles, Devices and Coatings

The SMP compositions can be used to prepare numerous articles of manufacture, for use in biomedical and other applications.

1. Articles and Devices for Biomedical Applications

The polymer compositions can be used to prepare articles of manufacture for use in biomedical applications. For example, sutures, orthodontic materials, bone screws, nails, plates, catheters, tubes, films, stents, orthopedic braces, splints, tape for preparing casts, and scaffolds for tissue engineering, contact lenses, drug delivery devices, implants, and thermal indicators, can be prepared.

The SMP compositions are preferably prepared from biocompatible polymers, and, for most applications, from biodegradable polymers. Biodegradable polymers degrade at a controlled rate depending on the composition and crosslinking of the polymer. Degradable polymeric implants eliminate the need for implant retrieval and can be used simultaneously to deliver therapeutic agents.

The materials can be used in many applications requiring load-bearing capacities and controlled degradation.

The polymer compositions can be formed into the shape of an implant which can be implanted within the body to serve a mechanical function. Examples of such implants include rods, pins, screws, plates and anatomical shapes.

A particularly preferred use of the compositions is to prepare sutures that have a rigid enough composition to provide for ease of insertion, but upon attaining body temperature, soften and form a second shape that is more comfortable for the patient while still allowing healing.

Another preferred use is in the area of catheters. A catheter can be rigid at body temperature for ease of insertion, but, after warming to body temperature, can soften to provide comfort to the patient.

The polymer compositions can be combined with fillers, reinforcement materials, radioimaging materials, excipients or other materials as needed for a particular implant application. Examples of fillers include calcium-sodium-metaphosphate which is described in U.S. Pat. No. 5,108, 755, the disclosure of which is incorporated herein by reference. Those of skill in the art can readily determine a suitable amount of these materials to include in the compositions.

The articles can incorporate various therapeutic and/or diagnostic agents, as described above.

2. Non-Medical Applications

There are numerous applications for the shape memory polymer compositions other than biomedical applications.

Examples of non-medical type applications for biodegradable polymers include items for which disposal is an issue, such as disposable diapers and packaging materials.

3. Coatings with controlled degradation

Shape memory polymers can be designed so that the degradation rate is varied. For example, in one embodiment, a hydrolytically degradable polymer can be selectively protected by applying a hydrophobic SMP coating that temporarily prevents water from reaching the hydrolytically cleavable bonds of the bulk polymer. The protective feature of the coating then can be modified when desired by applying an external stimulus such that the diffusion properties of coating are altered to permit water or other aqueous solutions to permeate through the coating and initiate the degradation process. If the hydrolysis rate is relatively high compared to the diffusion rate of water, then the diffusion rate of water through the coating determines the degradation rate. In another embodiment, a hydrophobic coating consisting of densely crosslinked soft segments can be used as a diffusion barrier for water or aqueous solutions. The soft segments should be at least partially crosslinked by linkages that can be cleaved by application of a stimulus. The diffusion rate of water can increased by lowering the crosslinking density.

VII. Methods of Use

Certain articles of manufacture are designed to hold their intended shape unless acted upon in a manner inconsistent with their normal use. For example, a car bumper will hold its intended shape unless it has been impacted. These articles of manufacture are to be used in their intended shape and repaired, for example, by application of heat, once they are damaged.

Other articles of manufacture are designed to be used such that the first shape is intended for an initial use, and a second shape is intended for a subsequent use. Examples of these include biomedical devices which can form a second shape upon reaching at body temperature, or upon application of an external stimulus which heats the device above body temperature.

Still other articles of manufacture are designed to be used such that their shape changes in reaction to, or adjustment to, changes in temperature, such as thermosensers in medical devices.

The present invention will be further understood with reference to the following non-limiting examples.

Example 1

Copolyesterurethane Shape Memory Polymers

A group of biocompatible and biodegradable multiblock-copolymers showing a thermal shape memory effect was synthesized. These polymers were composed of a crystallizable hard segment ($T_m$) and a soft segment having a thermal transition temperature $T_{trans}$ between room and body temperature. In contrast to the prior art segmented polyurethanes, the hard segment was an oligoester or an oligoetherester and did not contain any aromatic component.

Figure 6:
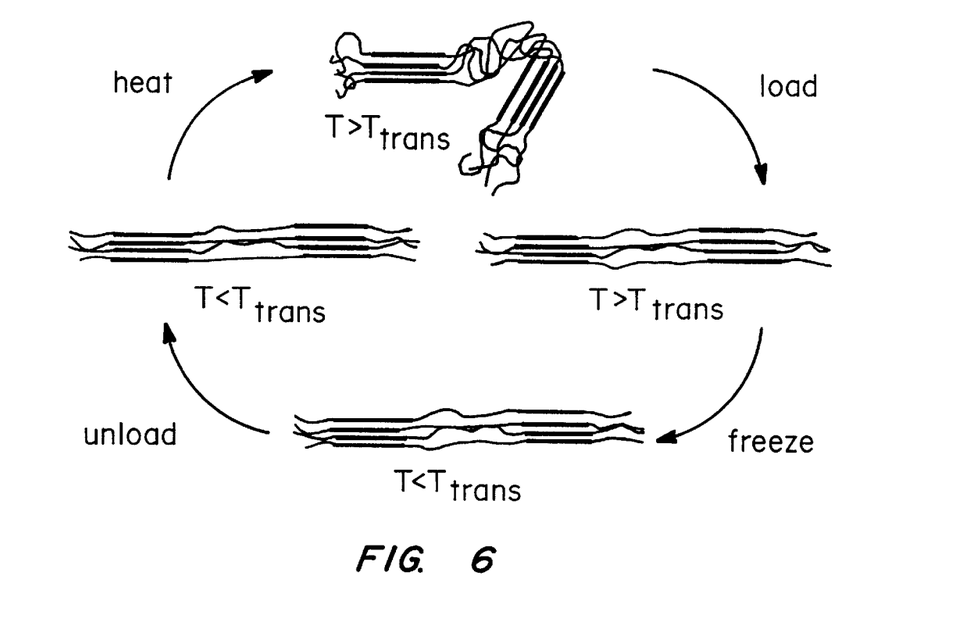
FIG. 6 is an illustration of the mechanism of the thermal shape memory effect for a multiblock copolymer.

The mechanism for programming the temporary shape and recovering the permanent shape of a multiblock-copolymer is shown in FIG. 6. The permanent shape of the materials was set by melting the polymer and cooling above $T_{trans}$ (FIG. 6—top pos.). Then, the polymer was formed into its temporary shape (FIG. 6—right pos.), which was fixed by cooling below $T_{trans}$ (FIG. 6—bottom pos.). After unloading, the permanent shape was recovered by reheating above $T_{trans}$. Synthesis of Telechelics, oligomers with functional groups at both ends.

The telechelic macrodiol were synthesized by ring opening polymerization of cyclic monomers with di(n-butyl) tinoxide as a transesterfication catalyst under a $N_2$ atmosphere.

Hard Segment

α,ω-dihydroxy [oligo(ethylene glycol glycolate) ethylene oligo (ethylene glycol glycolate)]—(PDS1200 and PDS1300) was prepared as follows. The monomer p-dioxane-2-one was obtained by distillation (thermal depolymerization) of the oligomer prior to use. 57 g (0.63 mol) of the monomer, 0.673 g (10.9 mmol) ethylene glycol, and 0.192 g (0.773 mmol) di(n-butyl) tinoxide were heated to 80° C. for 24 h. The end of the reaction (equilibrium) was determined by GPC. The product was soluted in hot 1,2-dichloroethane and filtered hot through a Buechner-funnel filled with silica gel. The product was obtained by precipitation in hexanes and dried in vacuo for 6 h.

Soft Segment i. Crystalline

Poly(ε-caprolactone)-diols with different $M_n$ are commercially available, for example, from Aldrich and Polysciences. PCL-2000 was used herein.

ii. Amorphous

α,ω-dihydroxy [oligo(L-lactate-co-glycolate) ethylene oligo (L-lactate-co-glycolate)]—(abbr.: PLGA2000-15) was prepared as follows. In a 1000 ml two-neck round bottomed flask, 300 g (2.08 mol) of L,L-dilactide, 45 g (0.34 mol) of diglycolide and 4.94 g (0.80 mol) ethylene glycol were heated to melt at 40° C. and stirred. 0.614 g (2.5 mmol) di(n-butyl) tinoxide was added. After 7 h, the reaction reached equilibrium as determined by GPC. The reaction mixture was soluted in 1,2-dichloroethane and purified in a silica gel column. The product was obtained by precipitation in hexanes and dried in vacuo for 6 h.

Properties of Telechelics

The molecular weight $M_n$ and thermal properties of the macrodiols were determined as shown in Table 1 below.

TABLE 1

Molecular Weight and Thermal Properties of the Macrodiols

| Label | $M_n$ GPC [g · mol$^{-1}$] | $M_n$ VPO [g · mol$^{-1}$] | $T_m$ [° C.] | ΔH [J · g$^{-1}$] | $T_g$ [° C.] | $\Delta C_p$ [J · g$^{-1}$] |
|---|---|---|---|---|---|---|
| PCL2000 | 1980 | 1690 | 43 | 73.5 | <−40 | — |
| PDS1300 | 1540 | 1340 | 97 | 74.5 | <−20 | — |
| PDS1200 | 2880 | 1230 | 95 | 75.0 | <−20 | — |
| PLGA2000 | 2020 | 1960 | — | — | 29.0 | 0.62 |

Synthesis of Thermoplastic Elastomers (Multiblock Copolymer)

In a 100 ml two-neck round-bottomed flask connected to a soxleth extractor filled with molecular sieve 0.4 nm, two different macrodiols (one hard segment and one soft segment) as described in Table 2 below were soluted in 80 ml 1,2-dichloroethane. The mixture was refluxed to dry by azeotropic extraction of the solvent. Freshly distilled trimethylhexane-1,6-diisocyanate was added with a syringe, and the reaction mixture was heated to 80° C. for at least 10 days. At regular intervals, samples of the mixture were taken to determine the molecular weight of the polymer by GPC. At the end of the reaction, the product was obtained by precipitating the polymer in hexanes and purified by repeatedly dissolving in 1,2-dichloroethane and precipitating in hexanes.

Multiblock copolymers were prepared from the following two types of polymers.

(i) PDC polymers contain poly(ε-caprolactone). $T_{trans}$ for the soft segment is the melting point.

(ii) PDL polymers contain a α,ω-dihydroxy [oligo(L-lactate-co-glycolate) ethylene oligo (L-lactate-co-glycolate)]. $T_{trans}$ for the soft segment is the glass transition point.

TABLE 2

Synthesis of Multiblock Copolymers

| Polymer | 1. Diol | m [g] | n [mmol] | 2. Diol | m [g] | n [mmol] | TMDI [mmol] | time [d] |
|---|---|---|---|---|---|---|---|---|
| PDC22 | PDS1200 | 3,0245 | 2,653 | PCL2k | 6,0485 | 3,024 | 5,738 | 10 |
| PDL23 | PDS1200 | 2,2787 | 2,000 | PLGA2k | 6.1443 | 3,070 | 5,163 | 10 |
| PDC27 | PDS1300 | 2,5859 | 1,724 | PCL2k | 5,3611 | 2,681 | 4,368 | 14 |
| PDC40 | PDS1300 | 3,6502 | 2,433 | PCL2k | 3,9147 | 1,957 | 4,510 | 13 |
| PDC31 | PDS1300 | 3,2906 | 2,194 | PCL2k | 4,8619 | 2,431 | 4,500 | 16 |
| PDL30 | PDS1300 | 3,7115 | 2,474 | PLGA2k | 4,0205 | 2,011 | 4,480 | 16 |

Properties of the Thermoplastic Elastomers

The physical, mechanical, and degradation properties determined for the compositions are provided in Tables 3–9 below.

The hydrolytic degradation behavior of the new materials were tested in buffer solution pH 7 at 37° C. It was shown that the polymers are completely degradable and their degradation rate can be adjusted by the concentration of easily hydrolysable ester bonds. The values for loss of relative mass $m_r = m(t_0)/m(t)$ in % at 37° C., and loss of relative molecular weight $M_r = M_w(t)/M_w(t_0)$ in % at 37° C.:

The toxicity of two different multiblock-copolymers was investigated using a chicken egg test. It was shown that blood vessels developed regularly and their condition was not influenced by the polymer samples.

TABLE 3

Composition of the Copolyester Urethanes Determined by 400 MHz $^1$H-NMR-Spectroscopy

| Label | Hard Segment | Weight Content [%]* | Soft Segment | Weight Content [%]* |
|---|---|---|---|---|
| PDL23 | PDS | 23.0 | PLGA | 54.2 |
| PDL30 | PDS | 30.0 | PLGA | 52.1 |
| PDC22 | PDS | 22.0 | PCL | 64.5 |
| PDC27 | PDS | 27.0 | PCL | 61.1 |
| PDC31 | PDS | 31.1 | PCL | 55.4 |
| PDC40 | PDS | 40.4 | PCL | 46.2 |

*The difference to 100% is the urethane content.

TABLE 4

Molecular Weight $M_W$ of the Copolyester Urethanes Films Determined by Multidetector-GPC

| | Polymer Film | | |
|---|---|---|---|
| Label | $M_W$(LS) [g · mol$^{-1}$] | $M_W$(Visc) [g · mol$^{-1}$] | dn/dc [ml · g$^{-1}$] |
| PDL23 | 161,500 | 149,000 | 0.065 |
| PDL30 | 79,100 | 83,600 | 0.057 |
| PDC22 | 119,900 | 78,500 | 0.078 |
| PDC27 | 72,700 | 61,100 | 0.080 |
| PDC31 | 110,600 | 108,600 | 0.065 |
| PDC40 | 93.200 | 86.300 | 0.084 |

TABLE 5

Transition Temperatures $T_m$ and $T_g$, Enthalpies of Fusion $\Delta H_m$ and Change in Heat Capacity $\Delta c_p$ of the Polymer Films from DSC Measurements (Values Given from Second Heating Process)

| Label | $T_{m1}$ [° C.] | $\Delta H_m^1$ [J · g$^{-1}$] | $T_g$ [° C.] | $\Delta C_p$ [J · g$^{-1}$] | $T_{m2}$ [° C.] | $\Delta H_{m2}$ [J · g$^{-1}$] |
|---|---|---|---|---|---|---|
| PDL23 | — | — | 34.5 | 0.38 | — | — |
| PDL30 | — | — | 33.5 | 0.25 | 85.0 | 8.5 |
| PDC22 | 35.0 | 26.0 | — | — | — | — |
| PDC27 | 37.0 | 25.0 | — | — | 75,5 | 3.5 |
| PDC31 | 36.5 | 28.5 | — | — | 76,5 | 5.5 |
| PDC40 | 35.0 | 7.0 | — | — | 77,5 | 7.0 |

TABLE 6

Mechanical Properties of Polymer Films at 50° C. from Tensile Tests

| Code | E-Modulus [MPa] | $\epsilon_r$ [%] | $\sigma_r$ [MPa] | $\epsilon_{max}$ [%] | $\sigma_{max}$ [MPa] |
|---|---|---|---|---|---|
| PDC27 | 1.5 | 1,350 | 2.1 | 1,300 | 2.3 |
| PDC31 | 1.5 | 1,400 | 4.9 | 1,300. | 5.4 |
| PDC40 | 4.0 | 1,250 | 5.8 | 1,300 | 5.9 |
| PDL30 | 2.0 | 1,400 | 2.1 | 1,250 | 2.3 |

TABLE 7

PDL22 Degradability

| Degradation Time [d] | $M_r$(viscosimetry) [%] | $M_r$(light scattering) [%] |
|---|---|---|
| 14 | 81.3 | 85.7 |
| 21 | 67.1 | 74.6 |
| 29 | 62.9 | 65.6 |
| 42 | 43.6 | 47.7 |
| 56 | 54.4 | 41.9 |

TABLE 8

PDL23 Degradability

| Degradation Time [d] | $M_r$(viscosimetry) [%] | $M_r$(light scattering) [%] |
|---|---|---|
| 14 | 61.1 | 87.3 |
| 21 | 40.7 | 76.7 |
| 29 | 32.8 | 62.2 |
| 42 | 17.4 | 46.7 |
| 56 | 16.9 | 18.5 |

TABLE 9

Loss of Relative Mass

| Degradation Time [%] | PDC22 m$_r$ [%] | PDL23 m$_r$ [%] |
|---|---|---|
| 14 | 99.2 | 98.1 |
| 21 | 99.3 | 97.5 |
| 29 | 98.6 | 97.2 |
| 42 | 98.3 | 96.9 |
| 56 | 97.3 | 93.3 |

Shape Memory Properties

Figure 7:
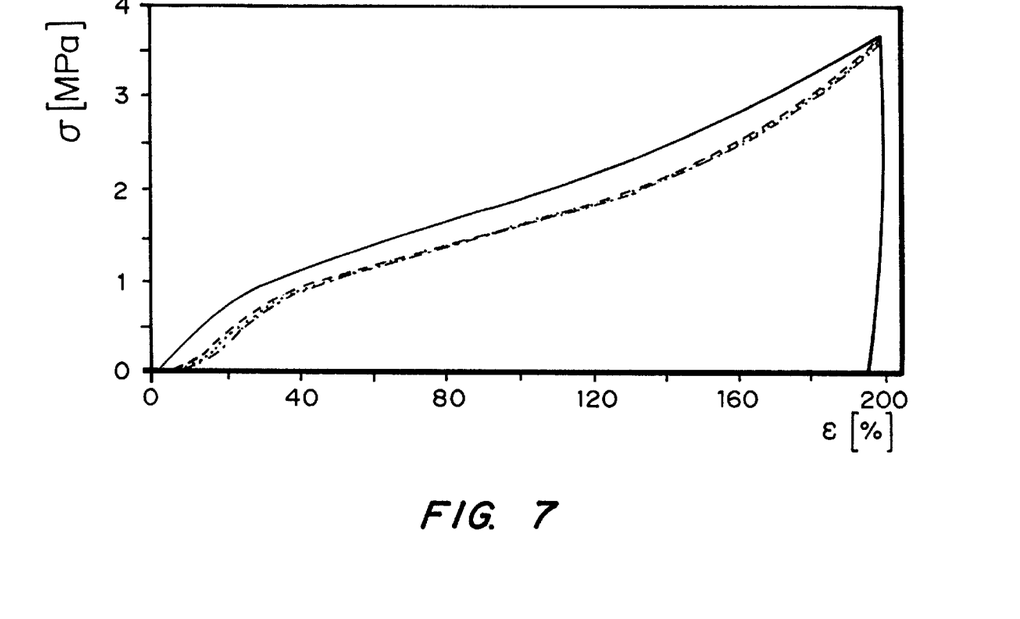
FIG. 7 is a graph showing stress versus elongation for a multi-block copolymer shape memory polymer.

FIG. 7 shows the results of tensile tests performed on the multiblock copolymers, as a function of the number of thermolytic cycles. The average shape fixity rate of thermocyclicly treated polymers and the dependency of strain recovery rates as a function of the number of cycles is shown below in Tables 10 and 11, respectively. The polymers have a high shape fixity, and an equilibrium state was achieved after only two cycles.

TABLE 10

Average Shape Fixity Rate R$_f$

| Label | Rf [%] |
|---|---|
| PDC27 | 97.9 |
| PDC40 | 96.2 |
| PDL30 | 97.7 |

TABLE 11

Cycle Number Dependence of Strain Recovery Rates R$_r$

| Number of Cycles | PDC27 R$_r$ [%] | PDC40 R$_r$ [%] | PDL23 R$_r$ [%] |
|---|---|---|---|
| 2 | 77.3 | 73.7 | 93.8 |
| 3 | 93.2 | 96.3 | 98.8 |
| 4 | 98.5 | 98.7 | 98.9 |
| 5 | 98.5 | 98.7 | 98.8 |

Example 2

Degradable Shape Memory Thermoset With Crystallizable Soft Segment

A range of poly(ε-caprolactone) dimethacrylates and thermosets were evaluated for their mechanical and shape memory properties.

Synthesis of Macromonomer

Poly(ε-caprolactone) dimethacrylates (PCLDMAs) were prepared as follows. To a solution of poly(ε-caprolactone) diol with M$_n$=2,000 gmol$^{-1}$ (20.0 g, 10 mmol) and triethylamine (5.3 mL, 38 mmol) in 200 mL of dry THF, methacryloyl chloride (3.7 mL, 38 mmol) was added dropwise at 0° C. The solution was stirred at 0° C. for 3 days and precipitated salt filtered off. After concentrating the mixture at room temperature under reduced pressure, 200 mL of ethyl acetate was added, and the solution filtered again and precipitated into a ten-fold excess of a mixture of hexanes, ethyl ether, and methanol (18:1:1). The colorless precipitate was collected, soluted in 200 mL of dichloroethane, precipitated again, and dried carefully at room temperature at reduced pressure.

Synthesis of Thermosets

The macromonomer (or the monomer mixture) was heated to 10° C. above its melting temperature (T$_m$) and filled into a mould formed by two glass plates (25 mm×75 mm) and a teflon spacer of 0.60 mm thickness. To achieve a good homogenity, the mould was stored at T$_m$ for another hour. Photocuring was performed on a heated plate at T$_m$ for 15 min. The distance between heat lamp head and sample was 5.0 cm. After cooling to room temperature, the sample was extracted and swollen with a 100-fold excess of dichloromethane overnight and washed carefully. Finally, the sample was dried at room temperature under reduced pressure.

Properties of Macromonomers and Thermosets

Table 12 below lists the poly(ε-caprolactone) dimethacrylates that were prepared, along with the respective degree of acrylation (D$_a$) (%) The number following PCLDMA is the molecular weight M$_n$ of the poly(ε-caprolactone) diol used in the synthesis as determined using $^1$H-NMR and GPC, rounded to 500.

TABLE 12

Poly(ε-caprolactone) Diol and Degree of Acrylation

| Name | D$_a$[%] |
|---|---|
| PCLDMA1500 | 87 |
| PCLDMA2000 | 92 |
| PCLDMA3500 | 96 |
| PCLDMA4500 | 87 |
| PCLDMA6500 | 93 |
| PCLDMA7000 | 85 |
| PCLDMA10000 | 86 |

Figure 8:
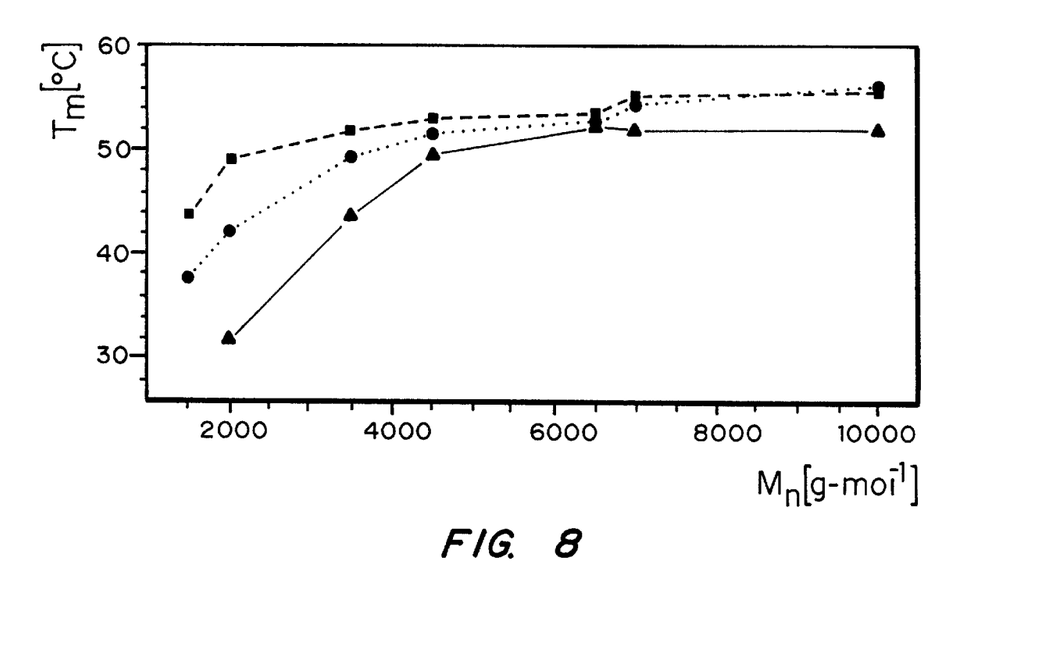
FIG. 8 is a graph showing the melting temperature of diols, dimethacrylates, and thermosets of poly(ε-caprolactone) as a function of the molar mass weight $M_n$ of the macromonomers.

FIG. 8 shows the melting temperature (T$_m$) of diols, dimethacrylates, and thermosets of poly(ε-caprolactone) as a function of the molar mass weight M$_n$ of the macromonomers. In the graph, macrodiols are represented by - -■- - ; macromoners by . . .●. . . ; and thermosets by —▲—.

The tensile properties of poly(ε-caprolactone) thermosets C1 through C7 at room temperature are shown below in Table 13, wherein E is the elastic modulus (Young's modulus), ε$_S$ is the elongation and σ$_S$ is the stress at the yield point, σ$_{max}$ is the maximum stress, ε$_{max}$ is the elongation at σ$_{max}$, ε$_R$ is the elongation at break, and σ$_R$, is the stress at break. Table 14 provided below shows the tensile properties of the same poly(ε-caprolactone) thermosets at 70° C.

TABLE 13

Thermoset Tensile Properties at Room Temperature

| name | E [MPa] | ε$_S$ [%] | σ$_S$ [MPa] | εmax [%] | σmax [MPa] | εR [%] | σ$_R$ [MPa] |
|---|---|---|---|---|---|---|---|
| C1 | 2.4 ± 0.6 | — | — | 16.1 ± 2.0 | 0.4 ± 0.1 | 16.1 ± 2.3 | 0.38 ± 0.02 |
| C2 | 35 ± 3 | — | — | 20.6 ± 0.3 | 4.7 ± 0.1 | 20.6 ± 0.3 | 4.7 ± 0.1 |

TABLE 13-continued

Thermoset Tensile Properties at Room Temperature

| name | E [MPa] | $\epsilon_S$ [%] | $\sigma_S$ [MPa] | $\epsilon$max [%] | $\sigma$max [MPa] | $\epsilon$R [%] | $\sigma_R$ [MPa] |
|---|---|---|---|---|---|---|---|
| C3 | 38 ± 1 | 48 ± 1 | 11.2 ± 0.1 | 180 ± 20 | 12.1 ± 1.2 | 190 ± 20 | 11.7 ± 1.6 |
| C4 | 58 ± 4 | 54 ± 1 | 12.2 ± 0.1 | 247 ± 4 | 13.6 ± 1.9 | 248 ± 13 | 15.5 ± 2.7 |
| C5 | 72 ± 1 | 56 ± 2 | 15.5 ± 0.2 | 275 ± 10 | 15.6 ± 1.7 | 276 ± 6 | 15.0 ± 1.0 |
| C6 | 71 ± 3 | 43 ± 2 | 14.2 ± 0.1 | 296 ± 14 | 15.5 ± 0.2 | 305 ± 8 | 13.8 ± 2.7 |
| C7 | 71 ± 2 | 42 ± 5 | 13.6 ± 0.2 | 290 ± 30 | 16.2 ± 0.5 | 290 ± 30 | 15.7 ± 0.9 |

TABLE 14

Thermoset Tensile Properties at 70° C.

| name | E [MPa] | $\sigma_{max}$ [MPa] | $\epsilon$R [%] |
|---|---|---|---|
| C1 | 1.84 ± 0.03 | 0.40 ± 0.08 | 24 ± 6 |
| C2 | 2.20 ± 0.12 | 0.38 ± 0.05 | 18 ± 2 |
| C3 | 6.01 ± 0.12 | 2.05 ± 0.21 | 43 ± 9 |
| C4 | 2.30 ± 0.16 | 0.96 ± 0.01 | 61 ± 3 |
| C5 | 1.25 ± 0.08 | 0.97 ± 0.15 | 114 ± 13 |
| C6 | 1.91 ± 0.11 | 1.18 ± 0.06 | 105 ± 11 |
| C7 | 0.70 ± 0.09 | 0.79 ± 0.10 | 210 ± 7 |

Shape Memory Properties

The thermosets were determined to have the thermomechanical properties indicated in Table 15. The number average molecular weights ($M_n$) is of the macromonomer. The lower limit temperature, $T_1$, is 0° C., and the higher limit temperature, $T_h$, is 70° C. The extension in the temporary shape is 50%. $R_r(2)$ is the strain recovery rate of the second cycle, $R_{r,tot}$ is the total strain recovery rate after 5 cycles, $R_f$ is the average strain fixity rate.

TABLE 15

Thermoset Thermomechanical Properties

| name | $M_n$ [g · mol$^{-1}$] | $R_r(2)$ [%] | $R_{r,\ tot}$ [%] | $R_f$ [%] |
|---|---|---|---|---|
| C4 | 4,500 | 93.3 | 93.0 | 93.9 ± 0.2 |
| C5 | 6,500 | 96.3 | 94.5 | 93.9 ± 0.2 |
| C6 | 7,000 | 93.8 | 92.1 | 92.5 ± 0.1 |
| C7 | 10,000 | 98.6 | 96.8 | 86.3 ± 0.5 |

Modifications and variations of the polymeric compositions and methods of preparation and use thereof will be obvious to those skilled in the art from the foregoing detailed description. Such modifications and variations are intended to come within the scope of the appended claims.

We claim:

1. A degradable shape memory polymer composition having at least one shape in memory, the polymer comprising
    (1) hard and soft segments or
    (2) at least one soft segment, which is crosslinked covalently or ionically, or
    (3) polymer blends,
    wherein the original shape of the polymer is recovered by a change in temperature or by application of another stimulus.
2. The composition of claim 1 comprising:
    a) at least one hard segment which has a $T_{trans}$ between −40 and 270° C.,
    b) at least one soft segment which has a $T_{trans}$ at least 10° C. lower than that of the hard segment(s), which is linked to at least one hard segment,
    wherein at least one of the hard or soft segments includes a degradable region or at least one of the hard segment (s) is linked to at least one of the soft segment(s) through a degradable linkage.
3. The composition of claim 2 wherein the $T_{trans}$ of the hard segment is in the range of between 30 and 150° C.
4. The composition of claim 3 wherein the $T_{trans}$ of the hard segment is in the range of between 30 and 100° C.
5. The composition of claim 2 wherein the $T_{trans}$ of the soft segment(s) is at least 20° C. below that of the hard segment(s).
6. The composition of claim 2 wherein at least one of the hard and soft segments is a thermoplastic polymer.
7. The composition of claim 2 wherein the hard segment comprises cyclic moieties.
8. The composition of claim 2 wherein the ratio by weight of the hard and soft segments is between about 5:95 and 95:5.
9. The composition of claim 1 wherein the shape memory polymer is selected from the group consisting of graft polymers, linear polymers, and dendrimer polymers.
10. The composition of claim 1 wherein polymer comprises a biodegradable region selected from the group consisting of polyhydroxy acids, poly(ether ester)s, polyorthoesters, poly(amino acids), synthetic poly(amino acids), polyanhydrides, polycarbonates, poly(hydroxyalkanoate)s, and poly(ϵ-caprolactone)s.
11. The composition of claim 1 wherein the polymer comprises a biodegradable linkage selected from the group consisting of ester groups, carbonate groups, amide groups, anhydride groups, and orthoester groups.
12. The composition of claim 1 wherein the polymer is completely degradable.
13. The composition of claim 1 comprising:
    a degradable thermoset polymer that comprises a covalently crosslinked crystallizable soft segment having a $T_m$ between 250° C. and −40° C. or a covalently crosslinked soft segment having a $T_{trans}$ 250° C. and −60° C.
14. The composition of claim 13 wherein the degradable thermoset polymer comprises a covalently crosslinked crystallizable soft segment having a $T_m$ between 200° C. and 0° C.
15. The composition of claim 1 comprising
    a) at least one first segment which has a $T_{trans}$ between −40 and 270° C.,
    b) at least one second segment which is linked to at least one first segment, and which comprises ionic interactions of sufficient strength that the second segment is able to form a physical crosslink other than a melting point or a glass transition, wherein at least one of the first or second segments includes a degradable region or at least one of the first segments is linked to at least one of the second segments through a degradable linkage.

16. The composition of claim 15 wherein the ionic interaction comprises polyelectrolyte segments or supramolecular effects based on highly organized hydrogen bonds.

17. The composition of claim 1 wherein the polymer has an inverse temperature effect, wherein the composition recovers its shape when cooled below its shape recovery temperature.

18. The composition of claim 1 wherein the polymer changes shape in response to light.

19. The composition of claim 1 wherein the polymer is a polymer blend.

20. The composition of claim 1 comprising a coating altering the degradation of the shape memory polymer.

21. An article comprising the biodegradable shape memory polymer composition of any of claims 1–20 or 26.

22. The article of claim 21 incorporating an agent selected from the group consisting of therapeutic, diagnostic and prophylactic agents.

23. The article of claim 21 wherein the article is implantable and the biodegradable shape memory polymer is biocompatible.

24. The article of claim 23 wherein the shape memory polymer does not contain aromatic groups.

25. The article of claim 21 wherein the article is a medical device selected from the group consisting of stents, catheters, prosthetics, grafts, screws, pins, pumps, and meshes.

26. The composition of claim 19 wherein the polymer blend is selected from the group consisting of physical mixtures of polymer, blends of polymers comprising hard segments with different Ttrans and soft segments having the same Ttrans, blends of multiblock copolymers wherein at least one of the segments of a first copolymer is miscible with at least one of the segments of a second copolymer, and blends of at least one multiblock copolymer and at least one homo or copolymer.

* * * * *